United States Patent [19]
Tajbl et al.

[11] 3,967,936
[45] July 6, 1976

[54] METHANATION PROCESS UTILIZING SPLIT COLD GAS RECYCLE

[75] Inventors: Daniel G. Tajbl, Evanston; Bernard S. Lee, Lincolnwood; Frank C. Schora, Jr., Palatine, all of Ill.; Henry W. Lam, Rye, N.Y.

[73] Assignee: The United States of America as represented by the United States Energy Research and Development Administration, Washington, D.C.

[22] Filed: Jan. 2, 1975

[21] Appl. No.: 538,061

[52] U.S. Cl. .......................... 48/197 R; 260/449 M
[51] Int. Cl.² ............................................ C10K 3/04
[58] Field of Search .......................... 48/197 R, 214; 260/449 M

[56] References Cited
UNITED STATES PATENTS

| | | | |
|---|---|---|---|
| 3,128,163 | 4/1964 | Weittenhiller et al. | 48/197 R |
| 3,511,624 | 5/1970 | Humphries | 48/197 R |
| 3,854,895 | 12/1974 | Muller | 48/197 R |
| 3,870,738 | 3/1975 | Yamamoto et al. | 260/449 M |

FOREIGN PATENTS OR APPLICATIONS

| 1,227,156 | 4/1971 | United Kingdom | 48/214 |
|---|---|---|---|

OTHER PUBLICATIONS
"Methanation of Coal Gas for SNG" Moeller et al. Hydrocarbon Processing Apr. 1974, pp. 69–74.

"Clean Fuels from Coal" Institute of Gas Technology Symposium Papers presented Sept., 1973, pp. 91–95, 109.

"Development of Catalysts and Reaction Systems for Methanation" Field et al. I and EC Research and Development June, 1964 pp. 150–153.

*Primary Examiner*—S. Leon Bashore
*Assistant Examiner*—Peter F. Kratz
*Attorney, Agent, or Firm*—Dean E. Carlson; A. F. Westerdahl

[57] ABSTRACT

In the methanation of feed gas comprising carbon monoxide and hydrogen in multiple stages, the feed gas, cold recycle gas and hot product gas is mixed in such proportions that the mixture is at a temperature sufficiently high to avoid carbonyl formation and to initiate the reaction and, so that upon complete reaction of the carbon monoxide and hydrogen, an excessive adiabatic temperature will not be reached. Catalyst damage by high or low temperatures is thereby avoided with a process that utilizes extraordinarily low recycle ratios and a minimum of investment in operating costs.

3 Claims, 1 Drawing Figure

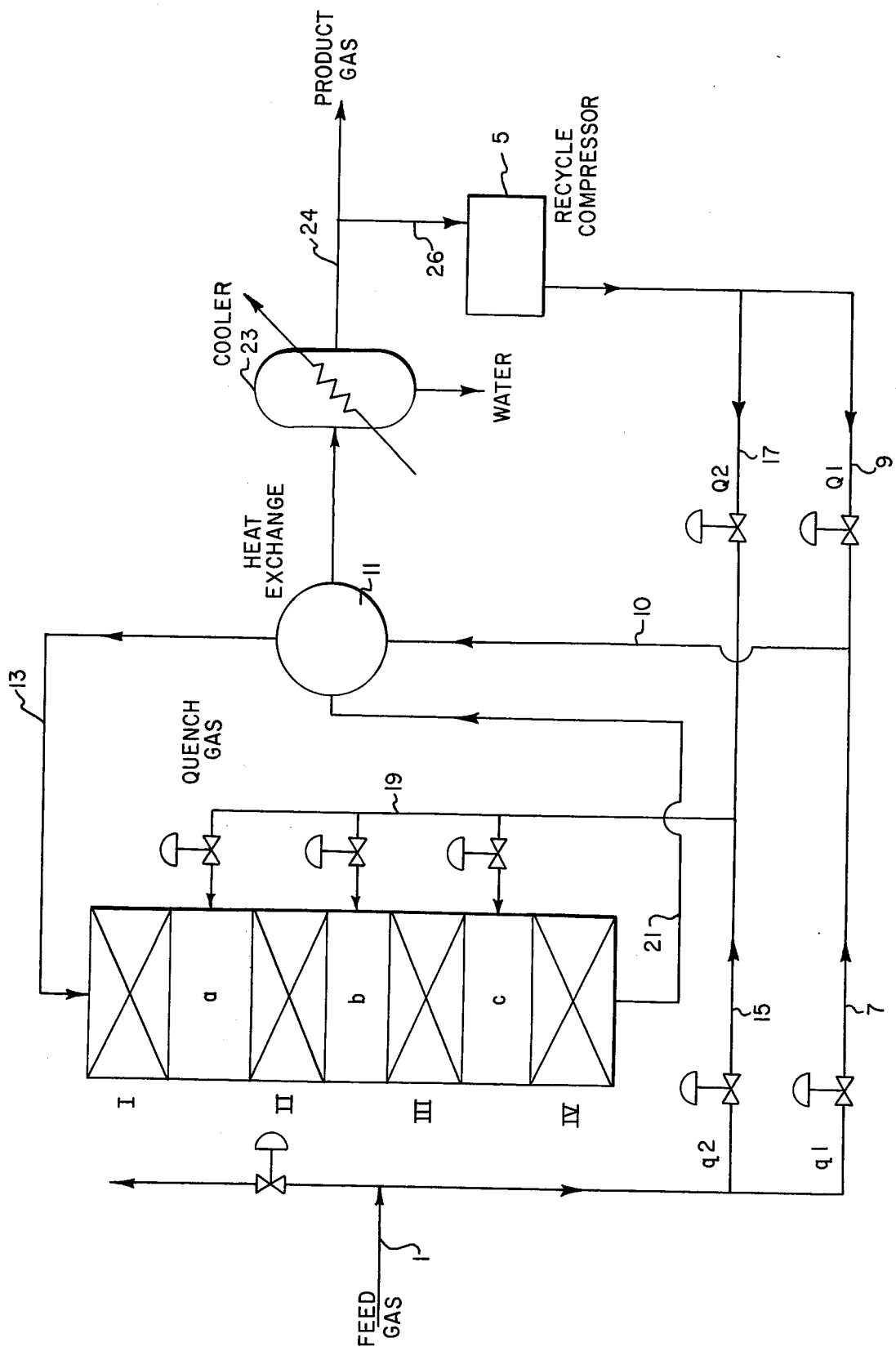

METHANATION PROCESS UTILIZING SPLIT COLD GAS RECYCLE

BACKGROUND OF THE INVENTION

1. Field of the Invention

This invention relates to the catalytic methanation of carbon oxides such as carbon monoxide.

2. Description of the Prior Art

In the fixed bed catalytic methanation of gases containing carbon monoxide and hydrogen, the reaction between the carbon monoxide and hydrogen is very exothermic and if not controlled within the reactor can cause overheating of the catalyst and/or thermal cracking of the product methane to carbon and hydrogen. Carbon formation through thermal cracking in turn has a tendency to foul the catalyst and plug up the gas passages in the catalyst bed. Also, it is important that the gas enter at a temperature sufficient to initiate the catalytic reaction of the carbon monoxide with hydrogen to form methane and to prevent the formation of a carbonyl compound which can occur through the reaction of the carbon monoxide with the catalyst at temperatures below proper operating temperatures.

To overcome some of these problems caused by overheating or carbonyl formation, a hot gas recycle method was developed by the U.S. Bureau of Mines (Industrial and Engineering Chemistry, Product Research and Development, 3, 150 (1964)). Also, direct cold gas recycle and internal cooling of the reactor by heat transfer surfaces within the bed are recognized methods by which temperature controls may be effected. Local heating is difficult to avoid when using the latter and the building of internal exchange surfaces tends to be expensive. The hot gas recycle and direct cold gas recycle methods on the other hand require high recycle ratios. As a consequence large pressure drops through the catalyst beds occur and the attendant requirement for compressor power is increased proportionately. In addition, despite the use of high recycle ratios there nevertheless is produced a "tail gas" of carbon oxides which indicates that conversion is not complete.

SUMMARY OF THE INVENTION

One object of the invention therefore is to provide a catalytic methanation process which is capable of effecting complete conversion of the carbon monoxide but which does not suffer from the drawbacks of the aforementioned methods.

Yet another object of the invention is to provide a methanation process wherein the desired conversion is obtained and the exothermic reaction is controlled without the need of expensive internally cooled surfaces or high recycle ratios.

A further object of the invention is to provide a methanation process wherein the catalyst damage by low or high temperatures is prevented with a minimum of investment and operating costs.

An additional object of the invention is to provide a methanation process wherein no interstage indirect heating or cooling is required and wherein the only heat exchange necessary is to heat the gas entering the first stage and cool the gases leaving the last stage.

These and other objects of the invention are obtained by the methanation of a feed gas comprised of carbon monoxide and hydrogen in a series of at least two catalytic reaction zones each of which is separated by a quench zone and wherein an effluent from each of said reaction zones, except the last zone, is passed through a quenched zone and into the succeeding reaction zone, which comprises splitting the feed gas into a first and a second feed, cooling product gas from the last of the reaction zones, splitting a portion of the cooled product gas into a first cold recycle gas and a second cold recycle gas, mixing the first cold recycle gas with the first feed gas, preheating said mixture of first feed gas and first cold recycle gas to a temperature sufficient to initiate the methanation reaction and prevent carbonyl formation on the catalyst, passing said gas mixture to the first reaction zone, the ratio of said first feed gas to said first cold recycle gas being selected to provide a gas mixture containing a carbon monoxide and hydrogen content which upon methanation produces insufficient heat to raise the gas temperature above the upper safe operating temperature of the catalyst in said first reaction zone, mixing said second feed and said second cold recycle gas to form a quench stream and passing said quench stream into said quench zones for admixture with the reaction zone effluent to provide a resultant gas mixture having a temperature sufficient to initiate the methanation reaction and prevent carbonyl formation on the catalyst, the ratio of said second feed gas to said second cold recycle gas being selected to provide a quench stream having a carbon monoxide and hydrogen content which upon methanation produces insufficient heat to raise the gas temperature above the upper safe operating temperature of the catalyst.

The process of the invention is carried out in a reactor system composed of two or more reaction zones or stages each of which contains a fixed bed of catalyst. The reaction stages may be combined in one vessel or they can be separate vessels. Between the catalyst is a quench zone which may be merely a pipe or conduit or other means whereby effluent may be passed from one reaction zone to the succeeding reaction zone.

The catalyst employed in the reactors may be any of the conventional hydrogenation catalysts employed in methanation processes. These catalysts include, for example, the iron-transition group metals, iron, cobalt, nickel, or a platinum group metal, e.g. platinum, palladium, rubidium and ruthenium, in the elemental or combined state, e.g. their oxides, sulfides or other inorganic form. Mixtures of these materials or compounds can be used if desired. Catalytic amounts of a catalyst on suitable supports such as alumina may be employed. The preferred catalysts are nickel and iron oxide.

Any number of catalytic zones or stages can be used, generally the greater the concentration of carbon oxides to be methanated the larger the number of stages. Ordinarily not more than about four stages will be used.

The feed gas compositions subjected to the methanation process of the invention are comprised of carbon monoxide and hydrogen and may include as well other gases such as methane, nitrogen, carbon dioxide, argon and the like. Illustrative of such gas feeds are hydrogasifier effluents which typically contain about 5 to 25 percent by volume of carbon monoxide and, 15 to 75 percent by volume hydrogen, 80 to 0 percent by volume methane and inert gaseous components.

By cold recycle gas as used herein and in the appended claims is meant product gas from the methanation cooled to 100°F or below, generally to about 70°F to 100°F.

In accordance with the process of the invention the composition of the gases entering the reactors is adjusted to a carbon monoxide and hydrogen content which when reacted or methanated will produce an amount of heat insufficient to raise the gas temperature above the upper safe operating temperature of the catalyst employed. This upper safe operating temperature varies from catalyst to catalyst and is known by those skilled in the art or easily determinable. In the case of nickel catalyst, for instance, the upper safe operating temperature is usually about 900°–950°F.

Thus, in the first reactor or reaction zone of the system, a mixture of feed gas and cold recycle gas is used with a carbon monoxide and hydrogen content sufficient to raise the mixture from its preheated inlet gas temperature to no higher than the upper safe operating temperature of the catalyst. The composition of the carbon monoxide and hydrogen in the feed gas/cold recycle gas mixture is regulated by adjusting the feed gas to cold recycle gas ratio such that adiabatic methanation of the carbon monoxide in the mixture to chemical equilibrium will create a rise in the gas mixture temperature to no higher than the upper safe operating temperature of the catalyst. The reaction will tend to zero rate at equilibrium and therefore preclude any uncontrollable situation. The temperature rise across the catalyst bed can be used to control the ratio of feed gas and cold recycle gas which in turn will vary as the carbon monoxide in the feed gas and the hydrogen in the product fluctuate. Therefore, at least one, usually the carbon monoxide of the feed gas, is continuously monitored so as to maintain the necessary carbon monoxide-hydrogen composition of the gas mixture to the initial reaction zone. It should be clear, therefore, that the feed gas/cold recycle gas ratio employed is dependent on a number of factors such as the cabon monoxide content of the feed gas, the hydrogen content of the recycle gas, the upper safe operating temperature of the catalyst employed, etc. In most instances, however, a ratio of feed gas to recycle gas that provides a gas mixture having a CO concentration of 4% and a hydrogen concentration of 12% is usually satisfactory.

Also in accordance with the process of the invention, a second mixture is prepared by mixing portions of the feed gas and cold recycle gas to provide a gas mixture having a carbon monoxide and hydrogen content such that when reacted or methanated the heat produced is sufficient to raise the temperature of the mixture, which is generally about 75° to 100°F to no higher than the upper safe operating temperature of the catalyst. As with the gas feed — recycle gas mixture to the initial reaction zone, the carbon monoxide-hydrogen composition of the quench stream is obtained by the regulation of the feed gas to cold recycle gas. This ratio is controlled by using the permissible temperature rise across the catalyst bed of the second and/or subsequent reaction zones and the aforementioned analyses of the carbon monoxide content of the feed gas and/or hydrogen content of the product gas continuously monitored. Again, as in the gas mixture passed to the initial reactor, the ratio of the feed gas to the recycle gas in the quench stream will vary for the same reasons but generally a ratio which provides a quenched stream having a CO concentration of 8% and a hydrogen concentration of 24% is satisfactory.

The quench stream thus prepared is then mixed with the effluent from the initial reaction zone and with effluents from subsequent reaction zones to quench the effluents. The proportion of quench stream delivered to each of the quench zones is that amount which will bring the resultant gaseous mixture to a temperature sufficient to both initiate the methanation and prevent carbonyl formation, that is, reaction of carbon monoxide with a catalyst.

The inlet temperature for each of the reaction zones will usually be similar and in any event a temperature at which the reaction initiates and carbonyl formation is prevented. The inlet temperature will vary primarily with the catalyst utilized and in the case of nickel catalyst, for instance, it will fall in the range of about 500° to 600°F.

The invention will be illustrated in further detail by reference to the attached drawing which is a schematic flow sheet of the process of the invention. Referring to the drawing, feed gas enters at 1 and is split into streams q1 and q2. Product gas is cooled to 100°F or below in cooler 23 to provide a cold recycle gas which is then split into streams Q1 and Q2. A recycle compressor 5 is used to recycle the split cold recycle gases. Feed gas stream q1 is passed by line 7 for admixture with cold recycle gas stream Q1 in line 9. The resultant gas mixture of Q1 and q1 is then passed through heat exchanger 11 wherein it is heated by heat exchange with product gas from the last reaction zone to a temperature sufficient to initiate the methanation reaction and prevent carbonyl formation. In general this temperature will range from about 500° to 600°F. The heat exchange gaseous mixture is then delivered by line 13 into the initial reactor designated I. The ratio of Q1/q1 is adjusted so as to obtain a gas mixture having a carbon monoxide content that upon complete reaction in reaction zone I will be capable of heating the gas from its preheated temperature at which it enters the reaction zone to no higher than the upper safe operating temperature of the catalyst utilized in the zone. Ordinarily this upper safe operating temperature will usually fall in the range of about 900°F–950°F.

In the same manner, feed gas stream q2 is passed via line 15 for admixture with cold recycle gas stream Q2 in line 17. The recycle ratio of Q2/q2 is now adjusted so that the temperature upon reaction of the carbon monoxide will give a temperature rise of from the temperature of the gaseous admixture of Q2 plus q2 which is usually about 100°F up to no higher than the upper safe operating temperature of the catalyst in the reaction zones. This gas mixture is then delivered by line 19 to quench zones designated a, b and c intermediate the reaction zones I and II, II and III, and III and IV, respectively, for quenching of the effluent that emerges from each of the reaction zones I, II and III. The rate of quench stream introduction is controlled so that the temperature of the gas mixture in the quench zones a, b and c is at that which will initiate the methanation reaction and at the safe lower operating temperature for the catalyst so as to prevent carbonyl formation.

In reactor systems with three or more stages or reaction zones the last stage will tend to use up any remaining gas from line 19. Should there be excess gas in line 19 which would tend to over cool the effluent in the quench zones, then the excess is sent to flare. Such a situation can be remedied by increasing the total flow to the reaction zone I. Product gas emerges by line 21 and is passed through or around heat exchanger 11, and into a cooler 23 with knock-out drum wherein water produced in the methanation step is removed.

Upon leaving the cooler 23 the product gas is removed by line 24 and a portion thereof for use as cold recycle is directed by line 26 to the recycle compressor 5. The product gas may be used to fire boilers or after drying to reduce the dew point can be placed into a pipeline and fed into a pipeline system.

EXAMPLE

In this example a two-stage system was employed rather than the four stage system zone of the drawing. Reaction zone I is a two foot diameter reactor packed with 5 feet of nickel catalyst pellet. Reaction zone II is a two foot diameter reactor packed with ten feet of nickel catalyst. Referring to the drawing feed gas in introduced at I and split into streams q1 and q2. Composition of the feed gas is shown in Table 1 below. Cold recycle gas from cooling means 23 is split into streams Q1 and Q2 also having the composition indicated in Table 1 below. Streams Q1 and q1 are admixed in a Q1/q1 ratio of 3 to 1, and directed by line 10 into heat exchanger 11 wherein the mixture is heated to a temperature of approximately 540°F and introduced into reaction zone I. The temperature 540°F is high enough to prevent nickel carbonyl formation between the nickel catalyst and the carbon monoxide in the gases yet is sufficiently high to initiate the methanation reaction.

Similarly, stream Q2 and q2 are mixed in a ratio of Q2 to q2 of 0.7 to 1 and introduced into quenching zone a for quenching of the gaseous effluent emerging from reaction zone I. The exit temperature from stage 1 is approximately 830°F which is below the upper temperature limit of operation of the nickel catalyst. The mixture of Q2 and q2 introduced into the quench zone for admixture with the effluent is introduced at a rate that brings the inlet temperature of the resultant gas mixture to approximately 540°F prior to introduction into reaction zone II.

The overall recycle ratio for the two stages is 1.45 parts of recycle gas per part of feed gas, (Q1 plus Q2)/(q1 plus q2). The temperature of the cold recycle gas was 88°F and the recycle compressor employed was a conventional compressor with conventional controls. The product gas rate was 21,600 standard cubic feet per hour and, the system pressure was at 932 psig.

The product gas composition is shown in Table 1 below.

| Gas Streams | q1 | q2 | Q1 | Q2 | Product |
|---|---|---|---|---|---|
| Composition, vol % | | | | | |
| $CH_4$ | 32.75 | 32.75 | 67.93 | 67.93 | 67.93 |
| $H_2$ | 37.60 | 37.60 | 6.56 | 6.56 | 6.56 |
| CO | 11.71 | 11.71 | 0 | 0 | 0 |
| $CO_2$ | 0 | 0 | 0 | 0 | 0 |
| $N_2$ | 17.80 | 17.80 | 25.28 | 25.28 | 25.28 |
| Ar | 0.09 | 0.09 | 0.17 | 0.17 | 0.17 |

It is seen from the Table that the product stream contains no carbon monoxide, indicating a complete conversion of carbon monoxide as fed to the methanation system. Also, in view of the unique selection of specific blends of recycle gas plus feed gas in a defined system of reactors according to the present invention the amount of recycle gas relative to feed gas is drastically reduced over the prior art method involving direct use of cold gas recycle or hot gas recycle. The recycle ratios of reported single stage cold gas recycle methods is 8 or 7 parts per part of feed gas whereas in hot gas recycle methods the main reactor recycle is about 20 to 1. With recycle ratios of this magnitude, the pressure drops through the catalyst beds is large and the attendant requirements for compressor power is increased proportionately. Furthermore, despite the use of large recycles in these prior art methods the final product has a tendency to produce a "tail gas" which shows small amounts of carbon monoxide and carbon dioxide. This indicates that the conversion is not complete despite the use of large recycles. In accordance with the process of the invention, on the other hand, full conversion of the carbon oxides is achieved with the use of the very much smaller recycles while simultaneously controlling the temperature of the reactors so that there can be no temperature hot spot in the bed or carbonyl formation which would damage the catalyst.

It is claimed:

1. A process for the methanation of feed gas in a series of at least two catalytic reaction zones each of said zones being separated by a quench zone wherein effluent from each of said reaction zones, except the last zone, is passed through a quench zone and into the succeeding reaction zone which comprises splitting said feed gas comprised of carbon monoxide and hydrogen into a first feed and a second feed, cooling product gas from the last of said reaction zones and splitting a portion of said cooled product gas into a first cold recycle gas and a second cold recycle gas, mixing said first cold recycle gas with said first feed gas, preheating said mixture of first feed gas and first cold recycle gas to a temperature sufficient to initiate the methanation reaction and prevent carbonyl formation and passing said gas mixture to the first reaction zone, the ratio of said first feed gas to said first cold recycle gas being selected to provide a gas mixture containing a carbon monoxide and hydrogen content which upon methanation produces insufficient heat to raise the gas temperature above the upper safe operating temperature of the catalyst in said first reaction zone, mixing said second feed gas and said second cold recycle gas to form a quench stream and passing said quench stream into the quench zone for admixture with the reaction zone effluent to provide a resultant gas mixture having a temperature sufficient to initiate methanation reaction and prevent carbonyl formation on the catalyst, the ratio of said second feed gas to said second cold recycle gas being selected to provide a quench stream having a carbon monoxide and hydrogen content which upon methanation produces insufficient heat to raise the gas temperature above the upper safe operating temperature of the catalyst.

2. The process of claim 1 wherin the catalyst is nickel.

3. The process of claim 2 wherein the inlet temperature of the gases in each reaction zone is about 500° to 600°F and the temperature of the effluent gases from each reaction zone is about 700° to 950°F.

* * * * *